(12) United States Patent
Guillermo et al.

(10) Patent No.: US 8,460,245 B2
(45) Date of Patent: Jun. 11, 2013

(54) DEVICE FOR DELIVERING A MEDICAMENT

(75) Inventors: Carlos Guillermo, Los Osos, CA (US); Lucio Giambattista, East Hanover, NJ (US); David DeSalvo, Lake Hiawatha, NJ (US)

(73) Assignee: SHL Group AB, Nacka Strand (SE)

( * ) Notice: Subject to any disclaimer, the term of this patent is extended or adjusted under 35 U.S.C. 154(b) by 272 days.

(21) Appl. No.: 12/666,963

(22) PCT Filed: Jul. 19, 2008

(86) PCT No.: PCT/EP2008/059493
§ 371 (c)(1),
(2), (4) Date: Jun. 13, 2010

(87) PCT Pub. No.: WO2009/010591
PCT Pub. Date: Jan. 22, 2009

(65) Prior Publication Data
US 2010/0249721 A1    Sep. 30, 2010

Related U.S. Application Data

(60) Provisional application No. 60/950,770, filed on Jul. 19, 2007.

(30) Foreign Application Priority Data

Dec. 5, 2007 (SE) .................................... 0702720

(51) Int. Cl.
*A61M 5/20* (2006.01)
*A61M 5/315* (2006.01)

(52) U.S. Cl.
USPC .......................... 604/135; 604/228

(58) Field of Classification Search
USPC ................. 604/187, 246, 245, 135, 192, 193, 604/198, 134, 218, 48, 228
See application file for complete search history.

(56) References Cited

U.S. PATENT DOCUMENTS 4,149,707 A   4/1979   Aronson
5,478,316 A   12/1995  Bitdinger et al.
(Continued)

FOREIGN PATENT DOCUMENTS

EP   0666084   8/1995
EP   0953122   11/1999
(Continued)

OTHER PUBLICATIONS

International Search Report for corresponding International Application No. PCT/EP2008/059493, dated Dec. 29, 2008.
(Continued)

*Primary Examiner* — Laura A Bouchelle
*Assistant Examiner* — Brooke Matney
(74) *Attorney, Agent, or Firm* — McDonnell Boehnen Hulbert & Berghoff LLP

(57) ABSTRACT

A device for delivery of medicament, which device comprises an elongated housing; a container (4) mounted within said housing and adapted to contain liquid medicament; a stopper slidably arranged within said container; and actuating means comprising a resilient member (60), a driving means (50) having one end connected to the stopper and a second end being operably connected to the resilient member, retaining means (40) for releasably retaining said driving means in a first position where said resilient member has an accumulated energy, and activating means operably connected to said retaining means for releasing said driving means to a second position, upon actively operation by an user, such that said accumulated energy is transferred to the driving means for driving the stopper a predetermined distance within the container whereby the medicament within said container i delivered characterized in that the resilient member is a variable force spring adapted for generating a predetermined sequence of at least two different force profiles during the medicament delivery.

9 Claims, 3 Drawing Sheets

U.S. PATENT DOCUMENTS

| | | |
|---|---|---|
| 5,988,452 A | 11/1999 | Dent et al. |
| 6,290,679 B1 | 9/2001 | Hostettler et al. |
| 7,112,187 B2 | 9/2006 | Karlsson |
| 7,125,395 B2 | 10/2006 | Hommann et al. |
| 7,828,770 B2 * | 11/2010 | Bivin et al. .................. 604/132 |
| 2007/0021720 A1 | 1/2007 | Guillermo |
| 2007/0112310 A1 | 5/2007 | Lavi et al. |

FOREIGN PATENT DOCUMENTS

| | | |
|---|---|---|
| JP | 63-130938 | 6/1988 |
| WO | 94/21316 | 9/1994 |
| WO | 98/30811 | 7/1998 |
| WO | 2004/028598 | 4/2004 |
| WO | 2006/057604 | 6/2006 |

OTHER PUBLICATIONS

Written Opinion for corresponding International Application No. PCT/EP2008/059493, Dec. 29, 2008.

* cited by examiner

DEVICE FOR DELIVERING A MEDICAMENT

TECHNICAL FIELD

The present invention relates to a device for the delivery of medicament to a patient. The device is adapted to be in a medicament delivery state and in a medicament non-delivery state. When the device is in a medicament delivery state, said device is adapted to drive a plunger into a container containing the medicament to be delivered, with a predetermined sequence of at least two different force profiles.

BACKGROUND ART

Devices for the delivery of medicament in an automatic way e.g. auto-injectors, are known as convenient and safe aids for patients to administrate various drugs themselves. For safety reasons, many devices for the delivery of medicament include covers and other devices that protect users before and after use, for example, from an injection needle. Although different devices for the delivery of medicament vary in their total feature sets, they all have a mechanism that delivers the contents of a preloaded, prefilled container automatically, i.e., without requiring a person to manually force the contents within a container through a delivery member e.g. a needle, a nozzle, into the patient.

Autoinjectors are described in U.S. Pat. No. 5,478,316 to Bitdinger et al.; U.S. Pat. No. 7,112,187 to Karlsson; and U.S. Pat. No. 7,125,395 to Hommann et al.; U.S. Patent Application Publication No. 200710021720 to Guillermo; and International Publication No. WO 20061057604 A1 by Olson, for example.

The automatic delivery mechanism in a device for the delivery of medicament usually includes a compressed helical spring that drives a plunger rod forward as the spring decompresses upon activation of the device. In many cases, such springs work well. A fully compressed helical spring provides a force that is large enough to overcome the static friction between the plunger and the inner wall of a container, so called break loose force, and the spring at its full extension, which is often not at its full decompression, provides a force that is large enough to complete the injection stroke but causing the probability of the container breakage.

A challenge in the design of such springs is balancing the need for sufficient force at the end of stroke against the need for a not-too-large force during storage (when the spring is fully compressed) that may overload the other components in the device. Such other components may be made of plastics or similar materials that have limited strengths.

Thus, the drive mechanism in such a device for the delivery of medicament should meet the following simultaneous goals: 1) exert enough force to overcome the stopper's "break loose" force and initiate delivery of the medication, 2) exert enough force to complete-the injection stroke, 3) meet goals 1) and 2) in an acceptable time frame (usually a few seconds), and 4) exert a low force during storage.

Rather than use typical helical springs, some delivery devices use constant force springs. U.S. Pat. No. 5,478,316 cited above describes such a device.

Although constant-force springs are better able than compression helical springs to meet the design goals of such a device, they also come up short. During the processing of a prefilled container, the container is typically siliconized, i.e., given a coating of silicone, to ease the movement of the stopper during delivery. The silicone can be applied in a few different ways but all strive to distribute the silicone evenly—especially at the end of the container nearest the delivery member. Usually the silicone coating is thinner or lacking at the end of the barrel, with the result that the stopper's glide force increases towards.

Moreover, EP 0953122 A1 describes a coil spring of strip material having two portions of a non-uniform width and wherein each portion has a constant force characteristic. In the application of said coil spring to an injection device, the spring has a wide portion wound innermost which urges a syringe forwards for auto-penetration i.e. the penetration of the needle into an injection site, and a narrow portion which then takes over to eject the dose i.e. the auto-injection. The impelling of the syringe forwards has a greater force than that applied subsequently to a stopper of the syringe.

Although a coil spring of strip material having portions of a non-uniform width are better able than compression helical springs to meet the design goals of an autoinjector, they also come up with drawbacks. The design and the application of such a spring as described in EP 0953122 A1 leads to the drawbacks of painful penetration since a great force is used for this step, and of not exerting enough force to overcome the break-loose force at the end of the injection stroke.

SUMMARY OF THE INVENTION

The object of the present invention is therefore to provide an automatic medicament delivery device, which during medicament delivery applies a predetermined sequence of at least two different force profiles to a stopper, which ensures an optimal functionality of said device.

The present invention lowers the risk of damaging the container and/or the device during medicament delivery and reduces the problems with plastic deformation of the plastic materials of the delivery device in comparison with prior art automatic medicament delivery devices.

With the present invention it also possible to set a predetermined dose that is to be delivered in an easy and reliable way.

The inventors have recognized that the problems caused by typical compression helical springs and constant-force springs in medicament delivery devices can be overcome by a variable-force springs as described below.

These objects are accomplished with a delivery device according to the preamble of the independent claim(s) provided with the features according to the characterizing portions of the independent claim(s). Preferred embodiments of the present invention are set forth in the dependent claims.

According to a main aspect of the invention, it is characterized by a device for delivery of medicament, which device is adapted to comprise an elongated housing; a container mounted within said housing and adapted to contain a liquid medicament; a stopper slidably arranged within said container; and actuating means comprising a resilient member, a driving means having one end connected to the stopper and a second end being operably connected to the resilient member, retaining means for releasably retaining said driving means in a first position where said resilient member has an accumulated energy, and activating means operably connected to said retaining means for releasing said driving means to a second position, upon actively operation by an user, such that said accumulated energy is transferred to the driving means for driving the stopper a predetermined distance within the container whereby the medicament within said container is delivered characterized in that the resilient member is a variable force spring adapted for generating a predetermined sequence of at least two different force profiles during the medicament delivery.

According to another aspect of the present invention, the last force profile in said sequence is a profile where the force increases.

According to a further aspect of the present invention, the variable force spring is a coil spring of band material and wherein the different force profiles are obtained by suitably adjusting the material and/or the geometry and/or the natural radius and/or the elastic modulus of the spring.

According to yet another aspect of the present invention, the variable force spring has one end attached to a carrier which is fixedly arranged to the housing and a second end, which is variably wound, cradled on the second end of the driving means.

According to a further aspect of the present invention, the activating means comprises a tubular member mounted to said housing and at least one resilient means operably connected to said tubular member, wherein said tubular member comprises an end portion adapted to be retractable with respect to said housing against the force of said resilient means when said end portion is pushed against a delivery site and wherein said tubular member is adapted to be urged in the direction of said end portion by the at least one resilient means when said end portion is removed from the delivery site.

According to yet another aspect of the present invention, the device further comprises dose setting means adapted to be operated in terms of predetermined steps when the device is in a medicament non-delivery state, wherein the operation of the dose setting means by one step increases the dose with a predetermined step.

These and other aspects of the invention and advantages with the present invention will become apparent from the following detailed description and from the accompanying drawings.

DETAILED DESCRIPTION OF THE INVENTION

In the present application, when the term "distal part/end" is used, this refers to the part/end of the delivery device, or the parts/ends of the members thereof, which under use of the delivery device, are located the furthest away from the medicament delivery site of the patient. Correspondingly, when the term "proximal part/end" is used, this refers to the part/end of the delivery device, or the parts/ends of the members thereof, which under use of the delivery device, are located closest to the medicament delivery site of the patient.

Traditional constant-force springs (CFSs) are coil springs of band material and often used when an application demands a smooth, even, uniform force through the entire expansion or contraction of the spring, e.g., the entire travel of a plunger through a container in a device for delivery of medicament e.g. an autoinjector. CFSs are commercially available from John Evans' Sons, Inc., Lansdale, Pa. 19446, USA, and Vulcan Spring & Mfg. Co., Telford, Pa. 18969 USA, for example.

With CFSs, force, or load, is a function of material width, thickness, and coil diameter. The load, which is directly proportional to the material width in a CFS and not directly proportional to material thickness, is given by the following expression:

$$P = Ebt^3 / 26.4R^2 \qquad \text{Eq. 1}$$

in which P is the load, E is the material's Modulus of Elasticity, b is the width of the material, t is the thickness of the material, and R, is the natural radius. If the elastic modulus is given in units of pounds per square inch (psi) and the material width, thickness, and natural radius are given in inches, then the load is given in pounds (lb).

Of course, other systems of units can be used.

The inventors have recognized that Eq. 1 can be used to design a variable-force spring (VFS), which is also coil spring of band material, having a predetermined profile of the load P by suitably adjusting the material and/or the geometry of the spring. Such VFSs are advantageous in devices for delivery of medicament e.g. autoinjectors, especially VFSs that exert a predetermined sequence of at least two different force profiles. There are three types of force profiles. A first force profile is a profile where the force decreases as the spring relaxes. A second force profile is a profile where the force increases as the spring relaxes. A third force profile is a profile where the force is constant as the spring relaxes. As just one of many possible examples, changing the radius of the coil, yielding a spring that exerts either increasing or decreasing force, is advantageous in a wide range of products, including devices for delivery of medicament.

Figure 1:
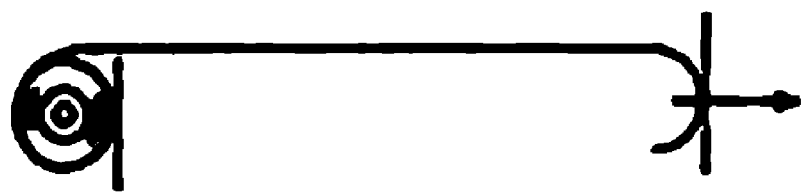
FIG. 1 illustrates a side cross-section view of a spring that exerts a load.

The inventors have also recognized that besides or instead of varying the natural radius, i.e., the radius of the coil, it is possible to make VFSs that exert a predetermined sequence of at least two different force profiles by modifying the other parameters in Eq. 1, e.g., the physical shape of the spring. Increasing, either the material's thickness or the width or both. FIG. 1 is a side cross-section view of a spring that exerts a load given by Eq. 1 and would be suitable for use in a device for delivery of medicament e.g, an autoinjector for example. The arrow in FIG. 1 indicates that an increasing force is needed to move the end of the spring further toward the right in the figure while the coil at the left remains stationary.

Figure 2:
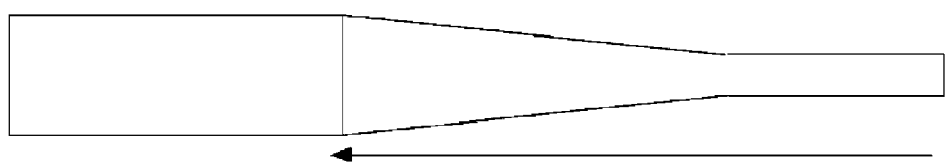
FIG. 2 illustrates a top view of material that, if wound into the shape of the spring depicted in FIG. 1.

FIG. 2 is a top view of material that, if wound into the shape of the spring depicted in FIG. 1 (except with the coil on the right in FIG. 3), would yield a spring that generates an increasing force as the spring relaxed. The varying width of the material will be noted in FIG. 2 as it is that variation that produces the desired load profile. The arrow in FIG. 2 indicates the direction of increasing force.

Figure 3:
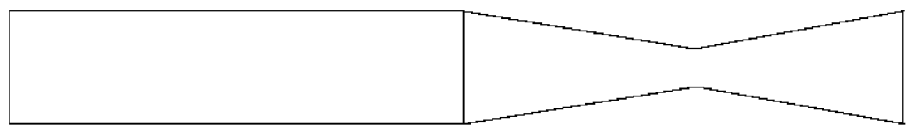
FIG. 3 illustrates a top view of a variable-force spring (VFS) that exerts a decreasing force and then an increasing force.

It will be understood that the parameters in Eq. 1 can be manipulated in various ways as necessary for the application of the VFS. For example, besides or instead of varying the width of the material, as depicted in FIG. 2, it is possible to vary the material's thickness and/or the elastic modulus. It will be noted that the load exerted by a VFS increases more by doubling the thickness than by doubling the width. The elastic modulus in different portions of the material can be varied in many ways, for example by selectively working the material in such portions, laminating other materials onto a base material in such portions, etc. Application requirements and manufacturing factors may indicate which parameter to vary, and such variation may be changed on a case-by case basis. For example, FIG. 3 is a top view of a VFS that exerts a decreasing force and then an increasing force. Thus, this is a VFS that exerts a predetermined sequence of at least two different force profiles.

Although it may be common to adjust the parameters for a new spring design, it is not common to adjust the parameters on each individual spring. The VFSs described above are advantageous in many applications. For example in devices for delivery of medicament e.g. autoinjectors having containers as syringes or cartridges pre-filled with liquid medicaments, where a variable force spring enables a predetermined sequence of at least two different force profiles applied to the stopper when the medicament is being delivered for overcoming problems due to siliconization profiles as at the end of the delivery stroke and/or for enabling a customized therapy as a delivery having multiple predetermined sequences of at least two different force profiles different force profiles. It should also be understood that variations in force can arise from other sources besides siliconization. The VFSs described above enable the spring forces generated to match or compensate the break-loose and glide force profiles within the container generated by different manufacturers and processes better than conventional springs.

Figure 4:
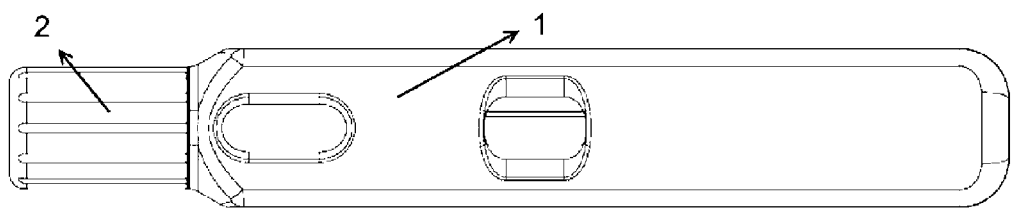
FIG. 4 illustrates a view of an assembled medicament delivery device that includes a VFS.
Figure 5:
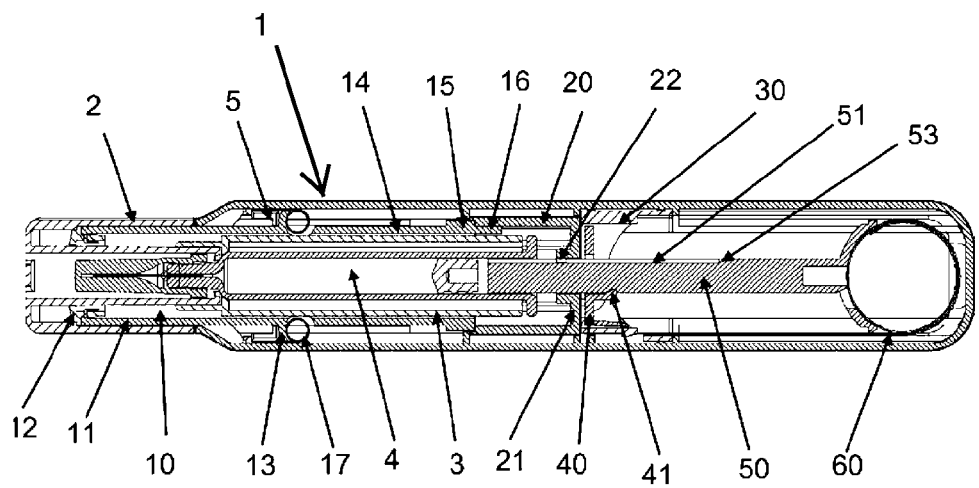
FIG. 5 illustrates a cross-section view of the medicament delivery device as in FIG. 4, FIG. 6, illustrates a cross-section of the medicament delivery device in FIG. 4 in a medicament non-delivered state.

FIG. 4 is a view of an assembled medicament delivery device that includes a VFS. FIG. 5 is a cross-section of the medicament delivery device as in FIG. 4, and FIGS. 6, 7, and 8 are cross-sections of the medicament delivery device in different states during use, which is described below.

As seen in FIG. 5, a device for delivery of medicament e.g. an autoinjector, comprises an elongated housing 1; a cap 2 mounted in the proximal end of the housing; a container 4 like a cartridge being adapted to receive a delivery member, or like a syringe, mounted within said housing and adapted to contain a medicament; a stopper slidably arranged within said container and actuating means for causing said stopper to slide with respect to said housing when the device is actuated from its medicament non-delivery state to its medicament delivery state. The actuating means comprises a resilient member which is a VFS 60; a VFS carrier 30, a driving means 50 like a plunger rod having one end connected to the stopper and a second end being operably connected to the VFS; retaining means 40 like a latch for releasably retaining said driving means in a first position where said VFS has an accumulated energy; and activating means 10 like a needle shield or like a button slidably positioned inside the housing and operably connected to said retaining means for releasing said driving means to a second position, upon actively operation by an user, such that said accumulated energy is transferred to the plunger rod for driving the stopper a predetermined distance with a predetermined sequence of at least two different force profiles whereby the medicament within said container is expelled, and wherein said activating means also comprises at least one resilient means 17 which function will be described below.

In a preferred embodiment, the container 4 comprises a delivery member in its proximal end and the cap 2 comprises a shield for protecting the delivery member. Moreover, the container 4 preferably comprises a flange at its distal end which abuts a periphery surface of a container housing 3 for preventing movement of the container.

In the preferred embodiment, the activating means is arranged as a tubular member 11. A portion of said tubular member extends outside the housing 1 towards the proximal end of the device completely covering the delivery member when the device is in a medicament non-delivery state. When the delivery device is arranged as an injector, then a penetration depth sleeve 12 is suitable arranged to the proximal end of the tubular member 11 for allowing the user to adjust the penetration depth of a needle. An outwardly annular ledge 13 extending radially from the distal end of the tubular member is arranged abutting a ledge 5 on the inner surface of the housing when the device is in a medicament non-delivery state. Further, the activating means also comprises two tongues 14 extending longitudinally towards the distal end of the device from the outwardly annular ledge 13. Said tongues 14 comprises on its outer surface a number of longitudinally equidistant ledges 15 which are adapted to engage corresponding grooves provide on the inner surface of a selector ring 20 when a predetermined dose of medicament to be delivered has been selected by the user. One of the tongues 14 comprises a tongue extension 16 extending towards the distal end of the device such that when the device is actuated from the medicament non-delivery state to the medicament delivery state, the tongue extension 16 passes through a through hole (not shown) which is arranged on a circumferential surface 21 of the selector ring 20.

In the preferred embodiment of the device at least one resilient means 17, two constant force springs, is arranged. These springs can also be replaced by another kind of resilient means e.g. a coil spring, a spiral spring. The wound ends of the spring 17 are cradle within the outwardly annular ledge 13 and the other end of the spring is secured to the housing.

In the preferred embodiment of the device, a dose setting means comprises at least one longitudinally stepped dose groove 51 with an end wall 53 arranged on the plunger rod 50. At least one of the longitudinally stepped dose grooves 51 is operably connected to an inwardly protrusion 22 arranged on a coaxial through hole on the circumferential surface 21 of the selector ring 20 wherein the plunger rod 50 is arranged to pass through. The distance between each end wall 53 and said protrusion 22 corresponds to a predetermined dose.

The proximal end of the plunger rod is arranged to be in contact with the stopper inside the container and the distal end the plunger rod is saddle formed for cradling the wound end of the VFS 60. The other end of the VFS is secured to the VFS carrier 30 which is fixedly arranged to inner surface of the housing 1. The retaining means 40 is pivotally arranged to the VFS carrier and comprises a protrusion 41 arranged to be in contact with a groove 52 of the plunger rod for holding the device in a medicament non-delivery state. The VFS carrier also comprises a through hole for allowing the plunger rod to pass through.

Figure 6:
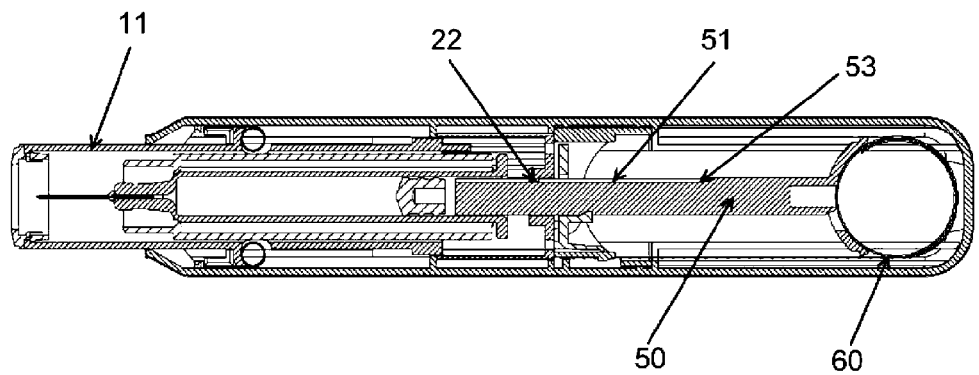

Before use, as seen in FIG. 6, the cap 2 is removed from the device and when the device is arranged as an injector, the penetration depth of the needle is set by handling the penetration depth sleeve 12 e.g. by pulling.

In the preferred embodiment the dose is set by operating i.e. rotating the selector ring 20 whereupon the protrusions 22 slides over the longitudinally stepped dose groove 51. Each time one of the protrusions 22 slides over the groove 51, the dose is predetermined increased. The set dose is indicated for the user by means of a dose indicating printing provided e.g. along the circumference of the exterior surface of the selector ring.

Figure 7:
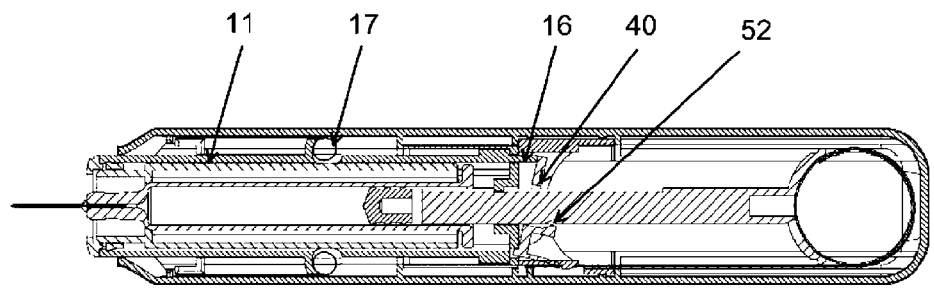
FIG. 7, illustrates a cross-section of the medicament delivery device in FIG. 4 in a medicament delivered state.

The delivery device is now ready to be set in a medicament delivery state as seen in FIG. 7. This is accomplished by pushing the tubular member 11 against a delivery site whereby when the device is arranged as an injector, the needle penetrates into the delivery site a predetermined depth and whereby the wound end of the constant force springs 17 rotates in the outwardly annular ledge 13 as the springs unravels. This movement is sufficient to displace the tongue extension 16 towards the distal end of the device, passing through the through hole which is arranged on the circumferential surface 21 of the selector ring 20 for pushing and thereby pivoting the retaining means 40. The pivoting of the retaining means 40 causes its protrusion 41 to come out of contact from the groove 52 arranged on the plunger rod 50. The plunger rod 50 is urged forwardly as the wound end of the VFS 60 rotates within the saddle of the plunger rod. The plunger rod now urges the stopper inside the container towards the proximal end of the device with a predetermined sequence of at least two different force profiles as fluid is displaced from the container through the delivery member. The movement of the plunger rod continues until the protrusion 22 of the selector ring engages the end wall 53 of the selected groove 51 on the plunger rod.

Figure 8:
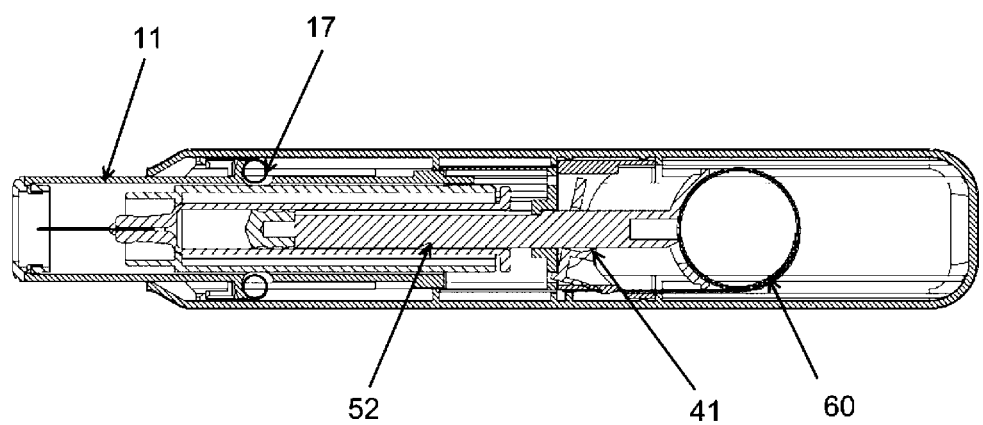
FIG. 8, illustrates a cross-section of the medicament delivery device in FIG. 4 in a final state.

Upon completion of the medicament delivery, the device is withdrawn from the delivery site and set in a final state as seen in FIG. 8. The activating means moves towards the proximal end of the device under the force of the springs 17 for covering the delivery member and the activating means is locked.

In a second embodiment, the activating means is arranged as a button (not shown) adapted for pivoting the retaining means 40. The pivoting of the retaining means 40 causes its protrusion 41 to come out of contact from the groove 52 arranged on the plunger rod 50.

However, even though the present invention has been described and illustrated in detail, said description and said illustrations shall be regarded as being non limited, since it will be appreciated that only the currently preferred embodiments have been shown.

The invention claimed is:

1. A device for delivery of medicament, comprising:
an elongated housing;
a container having a needle mounted within said housing and adapted to contain a liquid medicament;
a stopper slidably arranged within said container;
actuating means comprising a resilient member, and a plunger rod having a proximal end in contact with the stopper and a distal end being operably connected to the resilient member, a carrier fixedly arranged to an inner surface of the housing and configured not to move relative to the housing;
retaining means pivotally arranged to the carrier and comprising a protrusion arranged to be in direct contact with the plunger rod and be positioned in a groove of the plunger rod for releasably retaining the plunger rod in a first position where said resilient member has an accumulated energy, and activating means operably connected to said retaining means for releasing the plunger rod to a second position, upon active operation by an user, such that said accumulated energy is transferred to the plunger rod for driving the plunger rod and the stopper a predetermined axial distance within the container relative to the carrier that is fixed to the housing whereby the medicament within said container is delivered;
wherein the activating means comprises a tubular member mounted to the housing and at least one resilient means operably connected to the tubular member;
the tubular member comprises an end portion adapted to be retractable with respect to the housing against a force of the resilient means when the end portion is pushed against a delivery site such that the needle is penetrated into the delivery site;
the tubular member is adapted to be urged by a biasing force in an extended position in the direction of the end portion by the at least one resilient means when the end portion is removed from the delivery site;
the resilient member is not a helical compression spring but is a variable force spring having a first end that is directly connected to the carrier and a second end, which is variably wound, cradled on the second end of the plunger rod;
the variable force spring is adapted for generating a predetermined sequence of at least two different force profiles during the medicament delivery; and a last force profile in the sequence is a profile where force increases as the spring relaxes.

2. The device of claim 1, wherein the variable force spring is a coil spring of band material and wherein the different force profiles are obtained by adjusting at least one of the material and the geometry and the natural radius and the elastic modulus of the spring.

3. The device of claim 2, further comprising a dose setting mechanism adapted to be operated in predetermined steps when the device is in a medicament non-delivery state, wherein operation of the dose setting mechanism by one step increases the dose with a predetermined step.

4. The device of claim 3, wherein the dose setting mechanism comprises at least one longitudinally stepped dose groove with an end wall arranged on the driving means, wherein at least one of the longitudinally stepped dose grooves is operably connected to an inward protrusion arranged on a coaxial through hole on a circumferential surface of a selector ring where the driving means is arranged to pass through and wherein the distance between each end wall and said protrusion corresponds to a predetermined dose, such that when the device is in a medicament delivery state, the movement of the driving means stops when the protrusion of the selector ring engages the end wall.

5. The device of claim 2, wherein the tubular member comprises an outwardly annular ledge having two tongues extending longitudinally toward the distal end of the device; and one of the tongues comprises a tongue extension, such that when the end portion is pushed against a delivery site, the tongue extension pushes and pivots the retaining means causing the protrusion to come out from the groove.

6. The device of claim 5, further comprising a dose setting mechanism configured to be operated in predetermined steps when the device is in a medicament non-delivery state, wherein operation of the dose setting mechanism by one step increases the dose with a predetermined step.

7. The device of claim 6, wherein the dose setting mechanism comprises at least one longitudinally stepped dose groove with an end wall arranged on the driving means; at least one longitudinally stepped dose groove is operably connected to an inwardly protrusion arranged on a coaxial through hole on a circumferential surface of a selector ring where the driving means is arranged to pass through; and a distance between each end wall and the protrusion corresponds to a predetermined dose, such that when the device is in a medicament delivery state, the movement of the driving means stops when the protrusion of the selector ring engages the end wall.

8. The device of claim 1, further comprising a dose setting mechanism configured to be operated in predetermined steps when the device is in a medicament non-delivery state, wherein operation of the dose setting mechanism by one step increases the dose with a predetermined step.

9. The device of claim 8, wherein the dose setting mechanism comprises at least one longitudinally stepped dose groove with an end wall arranged on the driving means; at least one longitudinally stepped dose groove is operably connected to an inwardly protrusion arranged on a coaxial through hole on a circumferential surface of a selector ring where the driving means is arranged to pass through; and a distance between each end wall and the protrusion corresponds to a predetermined dose, such that when the device is in a medicament delivery state, the movement of the driving means stops when the protrusion of the selector ring engages the end wall.

* * * * *